United States Patent [19]

Wimmer et al.

[11] Patent Number: 5,030,770
[45] Date of Patent: Jul. 9, 1991

[54] PROCESS FOR THE PREPARATION OF THYMOL

[75] Inventors: Peter Wimmer; Hans-Josef Buysch, both of Krefeld; Lothar Puppe, Burscheid, all of Fed. Rep. of Germany

[73] Assignee: Bayer Aktiengesellschaft, Leverkusen, Fed. Rep. of Germany

[21] Appl. No.: 375,751

[22] Filed: Jul. 5, 1989

[30] Foreign Application Priority Data

Jul. 16, 1988 [DE] Fed. Rep. of Germany ....... 3824284

[51] Int. Cl.$^5$ .................... C07C 37/14; C07C 39/06
[52] U.S. Cl. .................... 568/781; 568/794; 568/781
[58] Field of Search .................... 568/781, 784

[56] References Cited

U.S. PATENT DOCUMENTS

| | | | |
|---|---|---|---|
| 1,886,311 | 11/1932 | Skraup et al. | 568/781 |
| 4,086,283 | 4/1978 | Biedermann et al. | 568/781 |
| 4,391,998 | 7/1983 | Wu | 568/781 |
| 4,405,818 | 9/1983 | Stead et al. | 568/781 |

FOREIGN PATENT DOCUMENTS 998186 7/1965 United Kingdom ............... 568/794

OTHER PUBLICATIONS

Soviet Inventions Illustrated, Sektion Chemie, Woche 8637, paragraph No. 244581, A 60, Sep. 26, 1986, Derwent Publications Ltd., London, GB; & Su-A-12 09678 (Moscow Gubkin Petrochem 2/7/86.
Bulletin of the Chemical Society of Japan, vol. 49, No. 10, Oct. 1976, pp. 2669–2673, Tokyo, Japan; T. Yamanaka; "Catalytic Properties of Metal Sulfates Supported on Gamma-A1203 in the Liquid-Phase Isopropylation of m-Cresol with Propylene" p. 2669, Column 1, lines 5–7.

*Primary Examiner*—Werren B. Lone
*Attorney, Agent, or Firm*—Sprung Horn Kramer & Woods

[57] ABSTRACT

Thymol can be prepared by reaction of m-cresol with propene at elevated temperature and at atmospheric to superatmospheric pressure by using wide- and medium-pored zeolites which have a pore diameter of at least 5 Å as heterogeneous catalysts.

16 Claims, No Drawings

PROCESS FOR THE PREPARATION OF THYMOL

BACKGROUND OF THE INVENTION

1. Field of the Invention The invention relates to a process for the preparation of thymol by reaction of m-cresol with propene on wide and medium-pored zeolites.

Thymol is important as odourant in the perfume industry, as antiseptic and also as component of pharmaceutical products. Moreover, it is the preferred starting material for the synthesis of menthol (Ullmanns Enzyklopädie der technischen Chemie [Ullmanns Encyclopaedia of Industrial Chemistry], 4th edition, volume 20, p. 241 and volume 18, p. 213).

2. Description of the Related Art Several processes for the alkylation of m-cresol with propene have been described in the literature. In these processes, apart from thymol mainly the isomeric isopropylmethylphenols and dialkylated and polyalkylated products are obtained (Ullmann, loc. cit., volume 18, p 204). According to DE-OS (German Published Specification) 2,528,303, thymol is prepared by alkylation of mcresol with propene in the liquid phase at 360°–365° C. and 48–50 bar over activated aluminas. The selectivity of thymol in the crude product is 80 %. Pure thymol is recovered from this product by fractional distillation. Calcium oxide (JP 45/15491 (1970)) and aluminium m-cresolate (GB 1,227,924) have also been described as catalysts for the synthesis of thymol. However, these catalysts only display useful activity and selectivity if the reaction is carried out in autoclave reactors under superatmospheric pressure.

In DE-AS (German Published Specification) 1,815,846, aluminium oxides which are impregnated with metal sulphates are described as catalysts. In this case, too, the reaction is carried out in the liquid phase in autoclaves. To achieve a conversion of 90–99 %, a three-fold excess of propene is required. The thymol selectivity is said to be 80–82 %, although it is not specified in this publication. In a publication written by the same author (Bull. Chem. Soc. Japan 49 (1976), 2669), similar data are presented. Using the already mentioned metal sulphate catalysts, good selectivities are only achieved with a three-fold excess of propene and conversions of 5–28 %. However, not all the by-products are included in the calculation of the selectivity. Since an increased formation of by-products takes place in the case of a high propene excess, the actual selectivities are clearly below the published values.

All these known processes have in common that, in order to achieve good conversions and selectivities, the reactions have to be carried out in the liquid phase under superatmospheric pressure, since the effect of the catalysts described is unsatisfactory under the conditions of atmospheric pressure. The resulting disadvantages are a consequence of the difficulties associated with carrying out reactions under pressure in industry.

For this reason, the gas phase propylation of m-cresol under atmospheric pressure has already been investigated. Using metal sulphates on alumina or silica support materials, maximum selectivities of 70 % are achieved in combination with conversions of up to 42 % (Bull. Chem. Soc. Japan 47 (1974), 2897). In addition to the low yield, the rapid deactivation of the catalyst described is another reason against its application in industry. In Bull. Chem. Soc. Japan 47 (1974), 2360, a γ-Al₂O₃ is described as a catalyst for the gas phase propylation of m-cresol under atmospheric pressure. The conversion is said to be 63 % and the thymol selectivity 90 %. According to the definition given, the calculation of the selectivity in this publication only refers to the thymol isomers. Polyalkylated compounds which amount to up to 10 % of the reaction product are not included in the calculation. As a result, the actual selectivity, that is, the relative percentage of thymol, based on all the reaction products, is considerably less than the values given. This has been confirmed by in-house comparative experiments using Al₂O₃ catalysts.

It was therefore desired to develop a process for the preparation of thymol from m-cresol and propene which can be carried out in the gas phase not only at atmospheric pressure but also at superatmospheric pressure and which furthermore gives good conversions and high selectivities in combination with long catalyst lives. Given the prior art, it was surprising and unforeseeable that the abovementioned disadvantages can be avoided by carrying out the reaction over the zeolite catalysts described below, which have a pore diameter of at least 5 Å (wide- and medium-pored zeolites).

SUMMARY OF THE INVENTION

A process for the preparation of thymol by reaction of m-cresol with propene at elevated temperature in the gas phase and atmospheric to superatmospheric pressure over heterogeneous catalysts has now been found, which is characterized in that the heterogeneous catalysts used are wide- and medium-pored zeolites which have a pore diameter of at least 5 Å.

Detailed Description of the Invention

Zeolite catalysts for the process according to the invention are covered by the formula

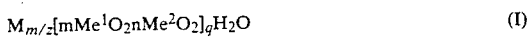

$$M_{m/z}[mMe^1O_2 nMe^2O_2]_q H_2O \qquad (I)$$

in which

M denotes an exchangeable cation,

Me¹ and Me² represent the elements of the anionic structure, n/m denotes the ratio of the elements and adopts values of 1–3,000, preferably 1–2,000, particularly preferably 1–1,000, z denotes the valency of the exchangeable cation and q represents the amount of the water adsorbed.

In terms of their basic structure, the zeolites are crystalline alumosilicates which are composed of a network of SiO₄ or AlO₄ tetrahedrons. The individual tetrahedrons are linked to one another with oxygen bridges via the edges and form a three-dimensional network, which is uniformly permeated by channels and hollow spaces. The individual zeolite structures differ in the arrangement and size of the channels and hollow spaces and in their composition. To neutralize the minus charge of the lattice, exchangeable cations are incorporated. The water phase qH₂O adsorbed can be removed reversibly without destroying the structure of the skeleton. In (I) Me¹ is in general aluminum, which can, however, be replaced by other elements, for example B, Ga, In, Fe, Cr, V, As or Sb. Furthermore, Me² in (I) is mainly silicon, which, however, can be replaced by other tetravalent elements, such as, for example, Ge, Ti, Zr or Hf. A detailed description of zeolites has been given, for example, in the monography by D. W. Breck "Zeolite Molecular Sieves, Structure, Chemistry, and Use", J. Wiley & Sons, New York, 1974.

The zeolites to be used according to the invention are wide- and medium-pored and have pore diameters of at least 5 Å, for example those in the range from 5 to 9 Å, preferably in the range from 5 to 7 Å.

Preferably, zeolites of the following structure types are suitable for the process according to the invention: erionite, faujasite, zeolite L, mordenite, mazzite, offretite, zeolite Ω, gmelinite, cancrinite, ZSM 12, ZSM 25 zeolite β, ferrierite, ZSM 5, ZSM 11, heulandite, ZSM 22, ZSM 23, ZSM 48, ZSM 43, ZSM 35, PSH 3, zeolite ρ, ZSM 38, CSZ 1, ZSM 3, ZSM 20 and chabasite, particularly preferably mordenite, zeolite Ω, ZSM 5, ZSM 11, ZSM 23, zeolite L, offretite, erionite and ferrierite. The zeolite types erionite, mordenite and ZSM 23 are very particularly preferred.

The zeolites can contain as exchangeable cations, for example, those of Li, Na, K, Mg, Cu, Ca, Zn, rare earth metals, Ti, Zr, Sn, Cr, Fe, Mn, Co, Ni and the like. According to the invention, those zeolites are preferred in which at least some of the metal ions have been exchanged for hydrogen ions, preferably 50-100 %, particularly preferably 80 to 100 %, of all metal cations which were originally present. The acidic H+ form of the zeolites is preferably prepared by exchanging metal ions for ammonium ions, followed by calcination of the exchanged zeolite. Another possibility in the case of zeolites which have an n/m value of 5 or greater consists in carrying out the proton exchange with mineral acids. Thus, in another preferred method the H+ forms of the zeolites of the structure type mordenite, ZSM 5, ZSM 23, erionite, zeolite Ω, offretite, zeolite L, ZSM 11 and ferrierite are used for the process according to the invention. Of these, the H+ forms of erionite, mordenite and ZSM 23 are particularly preferred.

The zeolite catalysts usually consist of the catalytically active zeolite component and a binder material. The latter is necessary to convert the zeolite into a form which is suitable for the process according to the invention. Suitable binder materials are, for example, $Al_2O_3$, $SiO_2$ or clay minerals. m-Cresol and propene are used in a molar ratio of 0.1-10, preferably 0.2-6, particularly preferably 0.5-2.

The process according to the invention is in general carried out in the gas phase at 1-5, preferably 1-2, bar and at a temperature of 150°-400° C., preferably 200°-300° C., particularly preferably 230°-270° C. However, the process according to the invention can also be carried out at superatmospheric pressure, for example in the range from about 5-50.

The total amount of the materials used is introduced into the reactor at a rate of 0.5-10 g/h per g of catalyst, preferably 3-5 g/h.

A favourable procedure for carrying out the process according to the invention consists in first passing m-cresol from a metering device into an evaporator. Propene in the desired molar ratio is added to the resulting vapour, and the gas mixture is passed through a heated reaction tube which contains the catalyst as a fixed bed. At the reactor outlet, the product mixture is condensed by cooling. The workup of the crude thymol is then carried out by fractional distillation. The starting material m-cresol which is recovered in the head fraction along with the isomeric thymols which have been separated off and the polypropylated by-products are recycled into the reactor. In this step, the isomer isopropylmethylphenols are isomerized to thymol and the polypropylated by-products are dealkylated to give thymol. This recycling of the reaction products which are not desired directly represents a preferred variation of the process according to the invention.

The zeolite catalysts are distinguished by a high catalyst life. If the activity of the catalyst after fairly long use slowly diminishes (for example by incipient coking), it can be regenerated by treatment with air at a temperature of 250°-800° C.; the catalyst regains its original activity in this treatment.

The zeolite catalysts are furthermore distinguished by high selectivity. The preferred variation of the recycling of the thymol isomers and polypropylated compounds leads to a further increase in the selectivity of thymol beyond the primary reaction products.

EXAMPLES

Description of the reactor and the general reaction procedure

The reactor consisted of a glass tube of 35 cm in length and an inner diameter of 25 mm, which was equipped with electric resistance heating. 10 g of the catalyst granules containing 30 % by weight of the binder material and having an average particle size of 1-2 mm was placed in the middle of the tube. The temperature in the catalyst packing was measured by means of a thermoelement. A layer of glass beads was placed above and below the catalyst packing. m-Cresol was introduced via a metering pump and transferred to the gas phase in an evaporator zone. Propene was introduced from a steel cylinder and the amount of gas added was determined by weighing. The condensible reaction products were condensed in a cold trap at 0° C. After the intervals given, samples for analysis by gas chromatography were removed.

The zeolites used in the examples below are characterized by the following $SiO_2/Al_2O_3$ ratios:

| Example | Zeolite type | $SiO/Al_2O_3$ |
| --- | --- | --- |
| 1a | H-ZSM 5 | 48 |
| 1b | H-ZSM 5 | 326 |
| 2 | H-offretite | 6.0 |
| 3 | H-zeolite Ω | 6.4 |
| 4 | H-erionite | 6.5 |
| 5 | H-ferrierite | 17.0 |
| 6 | H-ZSM 23 | 85 |
| 7a-f | H-mordenite | 16 |

EXAMPLES 1a-7f

A gaseous mixture consisting of m-cresol and propene was passed into the apparatus described above. The molar ratio of the reactants, the catalyst load and the temperature were varied, as explained in Table I below.

Experiment 7 is a long-term experiment. During its run, the molar ratio and the throughput of the reactants were varied.

EXAMPLE 8 (for comparison)

The reaction was carried out analogously to Examples 1a-7f. The result of analysis by gas chromatography is also shown in Table I.

TABLE I

| No. | Catalyst | m-Cresol/Propene | °C. | Throughflow rate (g/g/h) | Sample removed after h | Conversion (%)* | Selectivity (%)** |
|---|---|---|---|---|---|---|---|
| 1a | H-ZSM 5 | 1:1 | 250 | 3.5 | 6 | 34 | 75 |
| 1b | H-ZSM 5 | 1:1 | 250 | 3.5 | 3 | 25 | 72 |
| 2 | H-offretite | 1:1 | 250 | 3.5 | 6 | 30 | 71 |
| 3 | H-omega | 1:1 | 250 | 3.5 | 2 | 37 | 72 |
| 4 | H-erionite | 1:1 | 250 | 3.5 | 2 | 36 | 81 |
| 5 | H-ferrierite | 1:1 | 250 | 3.5 | 5 | 34 | 72 |
| 6 | H-ZSM 23 | 1:1 | 250 | 3.5 | 6 | 45 | 81 |
| 7a | H-mordenite | 1:1 | 250 | 3.5 | 4 | 44 | 82 |
| 7b | H-mordenite | 1:1 | 250 | 3.5 | 10 | 44 | 83 |
| 7c | H-mordenite | 1:1 | 250 | 3.5 | 16 | 44 | 84 |
| 7d | H-mordenite | 1:2 | 250 | 4.5 | 20 | 53 | 84 |
| 7e | H-mordenite | 2:1 | 250 | 3.0 | 28 | 30 | 87 |
| 7f | H-mordenite | 2:1 | 250 | 3.0 | 36 | 30 | 87 |
| 8 | ν-Al$_2$O$_3$ | 1:1 | 250 | 3.5 | 2 | 18 | 70 |

*based on m-cresol

**Selectivity = $\dfrac{\text{Mol \% of thymol}}{\text{Mol \% of all reaction products}} \times 100$ Table I shows the high selectivity of the zeolites used, in particular of H-mordenite, H-erionite and H-ZSM 23. Even at an unfavourable molar ratio of m-cresol/propene of 1:2, no deterioration of the selectivity compared to the molar ratio of 1:1 occurs.

Example 8 used as comparative experiment shows that activated γ-alumina (which is used in many industrial processes as highly active material) admittedly also has a catalytic effect under the conditions of the invention, but at a considerably lower conversion in combination with a relatively low selectivity with respect to the formation of thymol.

What is claimed is:

1. A process for the preparation of thymol by reaction of m-cresol with propene at a temperature of 150°-400° C. in the gas phase and at a pressure of 1-5 bar over heterogeneous catalysts, wherein the heterogeneous catalysts used are wide- and medium-pored zeolites which have a pore diameter of at least 5 Å.

2. The process according to claim 1, wherein the zeolites have a pore diameter of 5-9 Å.

3. The process according to claim 2, wherein the zeolites have a pore diameter of 5-7 Å.

4. The process according to claim 1, wherein the zeolites used are those of the type erionite, zeolite L, mordenite, mazzite, offretite, gmelinite, cancrinite, ZSM 12, ZSM 25, zeolite β, ferrierite, zeolite Q, ZSM 5, ZSM 11, heulandite, ZSM 22, ZSM 23, ZSM 48, ZSM 43 ZSM 35, PSH 3, zeolite ρ, ZSM 38, CSZ 1, ZSM 3, ZSM 20 and chabasite.

5. The process according to claim 4, wherein the zeolites used are those of type mordenite, ZSM 5, zeolite Q, ZSM 11, ZSM 23, zeolite L, offretite, erionite and ferrierite.

6. The process according to claim 5, wherein the zeolites used are those of the type erionite, mordenite and ZSM 23.

7. The process according to claim 1, wherein 50-100% of all exchangeable cations are present as H$^+$.

8. The process according to claim 7, wherein 80-100% of all exchangeable cations are present as H$^+$.

9. The process according to claim 7, wherein zeolites of the structure type mordenite, ZSM 5, ZSM 23, erionite, zeolite Ω, offretite, zeolite L, ZSM 11 and ferrierite are used in the H$^+$ form.

10. The process according to claim 9, wherein zeolites of the structure type erionite, mordenite and ZSM 23 are used in the H$^+$ form.

11. The process according to claim 1, wherein m-cresol and propene are used in a molar ratio of 0.1-10.

12. The process according to claim 11, wherein that m-cresol and propene are used in a molar ratio of 0.2-6.

13. The process according to claim 12, wherein that m-cresol and propene are used in a molar ratio of 0.5-2.

14. The process according to claim 1, characterized in that it is carried out at a pressure of 1-2 bar.

15. The process of claim 1, characterized in that the reaction is carried out at a temperature of 200°-300° C.

16. The process of claim 15, wherein the reaction is carried out at a temperature of 230°-270° C.

17. The process according to claim 1, wherein the by-products isolated from the crude reaction mixture are recycled into the reaction.

* * * * *

UNITED STATES PATENT AND TRADEMARK OFFICE
CERTIFICATE OF CORRECTION

PATENT NO. : 5,030,770

DATED : July 9, 1991

INVENTOR(S) : Wimmer et al.

It is certified that error appears in the above-identified patent and that said Letters Patent is hereby corrected as shown below:

Col. 5, claim 4 line 4   Delete " Q " and substitute -- $\Omega$ --

Col. 6, line 19   Delete " Q " and substitute -- $\Omega$ --

Col. 6, claim 12 line 1   Delete " that "

Col. 6, claim 13 line 1   Delete " that "

Col. 6, claim 14 lines 1-2   Delete " characterized in that " and substitute -- wherein --

Col. 6, claim 15 line 1   Delete " characterized in that " and substitute -- wherein --

Signed and Sealed this

Twenty-fifth Day of May, 1993

Attest:

MICHAEL K. KIRK

Attesting Officer

Acting Commissioner of Patents and Trademarks